United States Patent [19]

Powell

[11] Patent Number: 4,929,442

[45] Date of Patent: May 29, 1990

[54] COMPOSITIONS SUITABLE FOR HUMAN TOPICAL APPLICATION INCLUDING A GROWTH FACTOR AND/OR RELATED MATERIALS

[75] Inventor: Maxwell M. Powell, Great Neck, N.Y.

[73] Assignee: Exovir, Inc., Great Neck, N.Y.

[21] Appl. No.: 912,828

[22] Filed: Sep. 26, 1986

[51] Int. Cl.$^5$ ............. A61K 37/66; A61K 45/05; A61K 37/02

[52] U.S. Cl. .................. 424/85.2; 424/85.4; 424/85.7; 424/85.1

[58] Field of Search ............ 424/85.4, 85.5, 85.6, 424/85.7, 85.1, 85.2; 514/2, 12

[56] References Cited

U.S. PATENT DOCUMENTS

| | | | |
|---|---|---|---|
| 3,917,824 | 11/1975 | Camble et al. | 514/12 |
| 3,948,875 | 4/1976 | Cohen et al. | 530/399 |
| 4,373,519 | 2/1983 | Errede et al. | 128/156 |
| 4,507,281 | 3/1985 | Asculai et al. | 424/85.7 |
| 4,609,546 | 9/1986 | Hiratani | 530/351 |
| 4,621,052 | 11/1986 | Sugimoto | 530/399 |
| 4,743,679 | 5/1988 | Cohen et al. | 530/350 |

*Primary Examiner*—Blondel Hazel
*Attorney, Agent, or Firm*—Cooper & Dunham

[57] ABSTRACT

Compositions containing a tissue plasminogen activator (t-PA), epidermal growth factor (EGF), transforming growth factor-alpha (TGFα), transforming growth factor-beta (TGF-β), human endothelial cell growth factor (ECGF), granulocyte macrophage colony stimulating factor (GM-CSF) and a fibronectin or large external transformation sensitive protein (LETS) including cell surface protein (CSP), cell adhesion protein (CAP), cell insoluble globulin (CIG) and/or opsonic-alpha 2 surface binding glycoprotein in a suitable physiologically acceptable carrier are useful for the treatment of humans when topically and/or subcutaneously applied. These compositions might also usefully contain or have employed in association therewith an adjuvant to aid in the transdermal transport or transfer of the compositions, particularly the active components therein, through or across the skin. Also, these compositions might also have contained therein or employed in association therewith an antiviral agent, such as an antiviral surfactant, for example, an antiviral nonionic surfactant, e.g. nonylphenoxypolyethoxy ethanol and/or human interferon, e.g. alpha-interferon. Additionally, these compositions might contain or have employed in association therewith an antitumor agent, such as tumor necrosis factor (TNF), target cell lysis factor (TCLF) and carcino-breaking factor (CBF). These compositions are useful in the treatment or healing of humans, e.g. in the treatment of viral and/or cancerous skin disorders or lesions and/or to expedite healing.

12 Claims, No Drawings

COMPOSITIONS SUITABLE FOR HUMAN TOPICAL APPLICATION INCLUDING A GROWTH FACTOR AND/OR RELATED MATERIALS

BACKGROUND OF THE INVENTION

This patent application is related to the invention disclosed in copending, coassigned patent application Ser. No. 830,662 filed Feb. 18, 1986.

This invention relates to compositions and methods employing the same for the treatment and healing of humans. In one embodiment this invention relates to compositions and methods useful for the treatment of viral-associated skin disorders. In another embodiment this invention relates to the treatment of cancerous skin disorders. In yet another embodiment this invention relates to compositions useful for the treatment of humans to dissolve or remove blood clots.

Virus-caused skin disorders are known. Dermatropic viruses are known and include pox virus, measles virus, varicella-zoster virus, coxsackie virus, echovirus, herpes simplex virus, rubella adenovirus, pappilloma virus and molluscum-contagiosum virus. Skin disorders which are caused by viruses include exzema, conjunctivitis, psoriasis, keratoconjunctivitis, gingivostoma, herpes labium, herpes keratitis, genital herpes, chickenpox and shingles. Cancerous skin disorders are also known, such as melanoma, basal cell carcinoma, squamous cell carcinoma and Karposi sarcoma.

Various techniques nave been employed and compositions suggested for the treatment of the above-mentioned skin disorders. For example, surface active agents (surfactants) have been disclosed as being useful for the treatment of viral skin disorders, see U.S. Pat. No. 4,507,281. This patent also discloses that human interferon is advantageously employed in association with an antiviral surfactant in the treatment of herpes simplex viral infections. Interferon, a known antiviral agent, has also been suggested for use in the treatment of leukemia, a form of cancer. Also of interest as disclosing antiviral surfactants are U.S. Pat. Nos. 4,020,183 and 4,139,630.

Biologically active materials are known and have been suggested as being useful for the treatment of humans. For example, tissue plasminogen activator (t-PA), a blood clot dissolver or enzyme which converts or activates plasminogen into plasmin, is known, see, for example, *Biotechnology*, Vol. 4, August 1986, pp. 706–711 and *Genetic Engineering News*, Vol. 6, No. 7, July/August 1986, the article entitled "Competition Heats Up to Commercialize tPA for the Treatment of Heart Attack Patients" has been suggested for the treatment of heart attack victims. Other biologically active materials, such as epidermal growth factor (EGF), which stimulates the proliferation of various mammalian cells is known, see *Science*, Aug. 29, 1986, pp. 975–976. Another useful biological material for the control of proliferation and differentiation and other functions of cells, transforming growth factor-beta (TGF-$\beta$), is known, see *Science*, Aug. 1, 1986, pp. 532–534. TGF-$\beta$ would appear to have practical application in repair of injury caused by trauma, burns and surgery and debility in the aged, in addition to its ability to promote collagen formation. Other biologically active materials, transforming growth factor-alpha (TGF-$\alpha$), TGF-$\alpha$ and epidermal growth factor (EGF), are structurally related peptides and appear to be angiogenic mediators like epidermal growth factor, see *Science*, June 6, 1986, pp. 1250–1253. Another biologically active material useful in the practices of this invention is human endothelial cell growth factor (ECGF), see *Science*, Aug. 1, 1986, pp. 541–545. Still another biologically active material is fibronectin, see U.S. Pat. No. 4,585,654 and *Nature*, Vol. 321, June 19, 1986, p. /28. Fibronectin, also known as large external transformation sensitive protein (LETS), includes cell surface protein (CSP), cell aldhesion protein (CAP), cold insoluble globulin (CIG) and opsonic alpha 2 surface binding glycoprotein. Yet another biologically active material has been termed granulocyte macrophage colony stimulating factor (GM-CSF). This material has been identified as a glycoprotein of about 24–26,000 daltons and has been produced by employing recombinant genetic engineering techniques, see U.S. Pat. No. 4,230,697, PCT International patent application No. WO 85/04188 published Sept. 26, 1985, and *Science*, May 17, 1985, pp. 810–814. Of additional interest in connection with colony stimulating factor (CSF) are the publications, *J. Exp. Med.*, Vol. 152, October 1980, pp. 1036–1047, *Nature*, Vol. 314, Apr. 18, 1985, pp. 625–628, *Proc. Natl. Acad. Sci. U.S.A.*, Vol. 82, March 1985, pp. 1526–1530, *Exp. Hematol.*, Vol. 13, 1985, pp. 249–260, and *Blood*, Vol. 66, No. 4, 1985, pp. 788–795.

The disclosures of all the above-identified patents and publications and others mentioned hereinafter are herein incorporated and made part of this disclosure.

It is an object of this invention to prepare and utilize compositions containing one or more of the above-identified biologically active materials for the treatment of humans, for example, as antiviral and/or anticancer agents and/or a healing or cell growth agent.

It is another object of this invention to provide techniques for the employment of the above-identified biologically active materials in the treatment of humans.

How these and other objects are achieved will become apparent from the accompanying disclosure. In at least one embodiment of the practices of this invention at least one of the foregoing objects will be achieved.

SUMMARY OF THE INVENTION

In accordance with this invention, it has been discovered that biologically active materials, particularly compositions containing biologically active materials, are usefully and advantageously employed in the treatment of humans by topical application of these materials or compositions containing these biologically active materials. Biologically active materials which are usefully employed in accordance with the practices of this invention include tissue plasminogen activator (t-PA), epidermal growth factor (EGF), transforming growth factor-alpha (TGF-$\alpha$), transforming growth factor-beta (TGF-$\beta$), human endothelial cell growth factor (ECGF), granulocyte macrophage colony stimulating factor (GM-CSF), and a fibronectin or large external transformation sensitive protein (LETS) including cell surface protein (CSP), cell adhesion protein (CAP), cell insoluble globulin (CIG) and/or opsonic-alpha 2 surface binding glycoprotein.

The performance and/or activity and/or usefulness of these biologically active materials and compositions containing the same are enhanced and made more satisfactory and effective by incorporating an antiviral agent in compositions containing these biologically active materials or by employing an antiviral agent in association therewith. Suitable such antiviral agents include antiviral surfactants, such as antiviral nonionic surfactants, antiviral cationic surfactants and antiviral anionic surfactants. Particularly useful are the antiviral nonionic surfactants including nonylphenoxypolyethoxy ethanol, p-diisobutyphenoxypolyethoxy ethanol, polyoxyethylene (10) oleyl ether and onyx-ol. Other useful antiviral surfactants include the anionic surfactants, such as the sodium alkyl sulfonates and the sodium alkylbenzene sulfonates and the antiviral cationic surfactants including the quaternary ammonium surfactants, such as cetyl pyrimidinium chloride and benzalkonium chlorides.

Other antiviral agents usefully employed alone or in association with the compositions of this invention include human interferon, e.g. human alpha interferon or human leukocyte interferon, human beta interferon or human fibroblast interferon or human gamma interferon or human immune interferon. As indicated, these human interferons may be employed in a mixture with the above-mentioned antiviral surfactants in compositions in accordance with this invention which include one or more of the aforementioned biologically active materials.

In another special embodiment of the practices of this invention the aforementioned biologically active materials, e.g. TGF-$\alpha$, TGF-$\beta$, GM-CSF, EGF, t-PA, fibronectin and the related proteins LETS, CSP, CAP and CIG are usefully employed in the compositions of this invention in association with an antitumor agent and the like, such as tumor necrosis factor (TNF), interleukin (interleukin II) and other known antitumor agents including target cell lysis factor (TCLF) and carcinobreaking factor (CBF). Since human interferon is known to be an anticancer agent in addition to being an antiviral agent, a human interferon, such as human alpha interferon, is also usefully combined with the aforementioned antitumor agents in compositions in accordance with this invention or used in association therewith.

DETAILED DESCRIPTION OF THE INVENTION

The compositions in accordance with this invention containing a biologically active material, such as colony stimulating factor (CSF), are employed by topical application to the skin. Although topical application i.e. direct application, of the compositions of this invention to the skin is preferred, separate and sequential toplical application of the components of the compositions may be employed. A modified topical application might also be usefully employed wherein the compositions are applied subcutaneously, such as by direct injection into and/or under the skin.

In the compositions of this invention, the biologically active component, one or more, is in a form suitable for human application and treatment and is present or available and/or topically administered in an effective amount. With respect to the content of the biologically active material present in the composition, these materials are present, as indicated, in an effective amount, such as in an amount in the range 0.1-100 $\mu$g per gram of composition or in an amount in the range 0.0001-0.01% by weight of the composition. Higher and lower amounts might also be effectively employed in the practices of this invention.

As mentioned hereinabove, the compositions in accordance with this invention in addition to containing a biologically active material, such as t-PA or a CSF or EGF or TFG-$\beta$ or TGF-$\alpha$, also may usefully employ an antiviral agent in the composition or in association or in conjunction with the topical administration of the biologically active material. The preferred antiviral agents so employed are the human interferon antiviral nonionic surfactants mentioned hereinabove. Such antiviral surfactants serve to some extent a dual purpose. One purpose would be to enhance or improve the percutaneous transfer or transport of the biologically active material through the skin. The other purpose and effect of employing an antiviral surfactant would be attributable to its antiviral activity, which would be particularly useful in the instance where the lesion being treated or sought to be healed is caused by a virus or is the result of a viral infection, e.g. a herpes viral infection.

The amount of the antiviral surfactant employed in compositions of this invention would be any suitable effective antiviral amount, such as an amount in the range 0.1 to about 20% by weight of the composition containing the same. In the instance where the antiviral agent employed is a human interferon, such as human alpha interferon, alone or in combination with an antiviral surfactant, the amount of human alpha interferon in the compositions in accordance with this invention would be a suitable effective antiviral amount, such as an amount in the range $10^2$-$10^8$ I.U. per gram, or an amount in the range 0.00001-0.01% by weight. The presence of an effective antiviral amount of human interferon in association with a biologically active material in the compositions of this invention advantageously imparts antiviral properties to such compositions. Accordingly, such compositions would be especially useful in the treatment of viral skin lesions, e.g. herpes skin lesions, genital warts and the like, skin lesions due to shingles and cancerous skin lesions.

The compositions of this invention would also in some instances, if preferred, desirably include a material as an adjuvant which would aid in the transport or transfer or movement of the biologically active material through the skin when topically. Suitable such materials are known. For example, it is known that dimethylsulfoxide (DMSO) is useful as an agent for the transport of drugs and other material across or through the skin when such drugs or other materials are topically applied to the skin in the presence of dimethylsulfoxide. Other such adjuvants useful for the transport of the biologically active materials of this invention are known and include the glycols, such as polyethylene glycol, ethylene glycol and the like. Such adjuvants when included in compositions in accordance with this invention are employed in an effective amount, usually an amount in the range not more than 10% by weight of the composition, e.g. 1-5% by weight, effective to aid in the transport or movement of the biologically active material including interferon in the topically applied composition across or through the skin.

The compositions of this invention may be employed in any form suitable for topical application. For example, the compositions of this invention could be in liquid form or in lotion form, either oil-in-water or water-in-oil emulsions, in aqueous gel compositions, in the form of foams, sprays or suppository or in other forms embedded in a matrix for the slow or controlled release of the biologically active material to the skin or surface onto which it has been applied or in contact. Conveniently and usually, the compositions of this invention are aqueous compositions and preferably aqueous gel compositions and would contain therein not only the biologically active material but the other materials and adjuvants mentioned hereinabove. For example, the aqueous compositions and aqueous gel compositions of this invention would include not only the biologically active material, e.g. TGF-β, TGF-α, GM-CSF, but also an antiviral agent, such as an antiviral surfactant and a human inteferon, which is also an anticancer agent.

In accordance with a special embodiment of the practices of this invention, the compositions of this invention would also contain therein or be employed in association with known antitumor agents or anticancer agents. A preferred antitumor agent for use in compositions or in association with compositions of this invention is tumor necrosis factor (TNF). TNF is an antitumor agent, see *Proc. Natl. Acad. Sci. U.S.A.*, Vol. 72, No. 9, 1975, pp. 3666–3670. TNF while showing no or little toxic effect exerts a potent activity against tumors. TNF therefore is desirable as a component in compositions in accordance with the practices of this invention, particularly for the treatment of cancerous skin lesions, since it has no cytotoxic effect against normal cells while exhibiting significant antitumor activity.

Of interest with respect to the use of TNF as an antitumor or anticancer agent, see U.S. Pat. Nos. 4,309,418, 4,447,355, 4,457,916, 4,481,137, 4,495,282 and 4,529,594. For example, U.S. Pat. No. 4,481,137 discloses that several factors considered as promising therapeutic agents for tumors, e.g. lymphotoxin and TNF interferon, have been obtained from reticulo-endothelial cells and that carcino-breaking factor (CBF) as a mixture containing lymphotoxin and TNF has been obtained from a culture of lymphoblasts grown in immune-suppressed hamsters. U.S. Pat. No. 4,495,282 is also of special interest as disclosing another antitumor agent called target cell lysis factor (TCLF) as being comprised of lymphotoxin and human TNF.

In addition to or in association with TNF there might also be included in compositions of this invention another antitumor agent, a lymphotoxin, such as an interleukin, particularly interleukin II, see U.S. Pat. No. 4,518,584. Interleukin II has been demonstrated to be a useful antitumor agent and accordingly is especially useful for incorporation in compositions of this invention, together with one or more of the aforementioned biologically acceptable materials, e.g. GM-CSF, TGF-α, TGF-β, EGF, fibronectin and the like. All the above-mentioned materials including the antiviral surfactant, the very useful antiviral agent human interferon and any added adjuvant enhancing the transport or movement of these materials and the biologically active materials across or through the skin are present in effective out minor amounts in the compositions of this invention. Additionally, the other agents, particularly the antitumor or anticancer agents, such as TNF and interleukin II and related lymphotoxins, are also present in effective out minor amounts in compositions of this invention, such as amounts in the range 0.0001–0.01% by weight or an amount in the range 0.01 μg–100 μg per gram. These materials TNF and interleukin II and interferon may be natural or synthetic, e.g. produced by recombinant DNA technology.

The following are exemplary of preferred compositions in accordance with this invention, all embodied in an aqueous gel or in a water-dispersible lotion or other physiologically acceptable carrier in the form of a suppository, tampon, paste, tape or film support for controlled release of the biologically active materials and other materials incorporated therein.

| Biologically Active Component | Antiviral Surfactant | Interferon | Antitumor Agent | Other Adjuvant |
|---|---|---|---|---|
| t-PA | Nonylphenoxypolyethoxy ethanol | | | |
| TGF-α | | alpha Interferon | | |
| TGF-β | nonionic surfactant | alpha Interferon | Interleukin II | |
| TGF-β | nonionic surfactant | alpha Interferon | TNF | |
| t-PA | nonionic surfactant | | | dimethylsulfoxide |
| t-PA | nonionic surfactant | | | dimethylsulfoxide and a glycol |
| ECGF | nonylphenoxypolyethoxy ethanol | alpha Interferon | | |
| GM-CSF | nonionic surfactant | an interferon | Interleukin II | |
| fibronectin | nonionic surfactant | alpha Interferon | TNF and Interleukin II | glycol and an antimicrobial |
| fibronectin and CSF | nonionic surfactant | alpha Interferon and beta Interferon | TNF | |
| ECGF, fibronectin and TGF-α | nonionic surfactant | alpha Interferon | TNF, Interleukin II and lymphotoxin | |
| TGF-α, TGF-β and GM-CSF | nonionic surfactant | alpha Interferon and beta Interferon | TNF Interleukin II and lymphotoxin | an antimicrobial |
| t-PA, TGF-α or TGF-β, fibronectin | nonionic surfactant | alpha Interferon | Interleukin II | an antimicrobial |
| t-PA | | | | a material to enhance transfer of t-PA through skin |
| t-PA, | nonionic surfactant | | | DMSO and a glycol |
| t-PA, TGF-β, GM-CSF and fibronectin | nonionic surfactant | alpha Interferon or beta Interferon | TNF and/or Interleukin and/or lymphotoxin | an antimicrobial |

The compositions set forth hereinabove all contain the listed biologically active component in the form suitable for human use or application. The same is true with respect to those compositions which contain interferon, i.e. human interferon, employed in the listed compositions. Similarly, the antiviral surfactants and the antitumor agents employed are all suitable for human application, as well as the other materials employed in the compositions, specifically the other listed adjuvants.

As indicated hereinabove, the biologically active component is contained in the listed compositions in a suitable effective amount in the range 0.05-200 µg per gram of composition or an amount in the range 0.00005-0.05% by weight of the composition. Higher or lower amounts might also be effectively employed. The antiviral surfactant agents are usually employed in an amount greater than the amount of the biologically active component, such as an amount in the range 0.1% to 10-20% by weight.

Also, as indicated hereinabove, the interferon component and the antitumor component are usually employed in an amount the same as or in the same range as the biologically active component. The other materials making up the compositions of this invention, particularly the adjuvant materials, such as those materials which aid in the transport of the biologically active materials, the interferon and the antitumor agent, through the skin, which adjuvant materials might also usefully comprise an antibiotic or antimicrobial agent or an antiviral agent, are usually employed in an amount in the range 0.05-10% by weight of the composition, comparable to the amount of the antiviral surfactant therein, e.g. in a minor amount in the range 0.1-20% by weight.

The balance of the compositions comprises a substantially inert, physiologically acceptable carrier. The carrier should not react with the biologically active ingredients or other component so as not to reduce their effectiveness. Suitable physiologically acceptable, substantially inert carriers include water, an alkanol, e.g. ethanol, a polyethylene glycol, mineral oil or petrolatum, propylene glycol, dimethylsulfoxide, and the like. Dimethylsulfoxide is usefully included in the compositions since diemthylsulfoxide is known to effectively carry drugs through the skin and as such would be a useful component of the carrier in the compositions of this invention. The compositions of this invention, as indicated, are topically applied or administered in formulations suitable for topical application, such as gels, creams, lotions, shampoos, sprays and the like.

The following are examples of suitable formulations of carriers useful in the preparation of compositions in accordance with this invention:

| Pharmaceutical Lotion | |
| --- | --- |
| propylene glycol | 24.75 ml. |
| triethnolamine | 1.00 ml. |
| water | 7.00 ml. |
| oleic acid | 1.50 gm. |
| polyethylene glycol monostearate | 10.50 gm. |
| carbopol-934 (2% mucilage) | 50.00 ml. |
| Pharmaceutical Cream A | |
| white petrolatum | 41.00 gm. |
| microcrystalline wax | 3.00 gm. |
| fluid lanolin | 10.00 gm. |
| sorbitan monooleate | 4.75 gm. |
| polysorbate-80 | 0.25 gm. |
| purified water | 41.00 gm. |
| Pharmaceutical Cream B | |
| spermaceti | 7.5% |
| white wax | 12.0% |
| mineral oil | 56.0% |
| sodium borate | 0.5% |
| sorbitan monooleate | 5.0% |
| water | 19.0% |

Topical administration of compositions of the present invention may be effected by applying a small or adequate amount (e.g., about 1-10 mls or grams) of the compositions directly to and onto the areas of the site of the lesion and immediately adjacent thereto with a cotton swab, soft brush, sponge or the like. A quantity sufficient to cover the lesion or skin area to be treated is usually adequate. Treatment by topical application of the composition should be regular and, if necessary, frequent, for example, every 2-6 hours, for about 1-7 days, more or less.

The compositions of this invention could also possess antimicrobial activity as well as antitumor and antiviral activity. For example, the compositions are effective in treating serious skin bacterial infections and ulcers and the like when an antimicrobial agent is incorporated therein. As used herein, the term antimicrobial activity refers to activity against microorganisms other than viruses, such as bacteria, yeast and fungi.

In addition to direct topical application of the compositions, the compositions may be administered topically by various other methods, for example, when encapsulated in a temperature and/or pressure sensitive matrix or when encapsulated in a film or solid carrier which is soluble in body fluids and the like for subsequent release of the compositions. The compositions may also be delivered in foam, spray, tampon or suppository form.

In another embodiment, the compositions of this invention may also have cosmetic properties and/or include cosmetic materials. Cosmetic formulations are known in the art and are usually hypoallergenic and pH controlled. Cosmetic formulations in the compositions of this invention are especially useful for the treatment of cancerous and/or ulcerative skin disorders, particularly of the face. A typical carrier for use in a cosmetic formulation according the the present invention has the formulation:

| Cosmetic Cream | |
| --- | --- |
| beeswax | 12.1% |
| spermaceti | 12.6% |
| sweet almond oil | 54.4% |
| borax | 0.5 |
| rose water | 19.4% |

The following examples are further illustrative of the practices of this invention.

EXAMPLE 1

A composition in the form of an aqueous gel and containing GM-CSF in an amount of about 2.5 µg per gram of composition which also contains 2% by weight nonylphenoxypolyethoxy ethanol and human alpha interferon and interleukin II in an amount of about 0.5 µg each per gram of composition is applied to a cancerous skin lesion, such as a melanoma, sufficient to generously cover the lesion. After 4-6 hours another similar application is made and this procedure continued for 4 days and then discontinued for observation and evaluation before another such series of treatment.

EXAMPLE 2

A composition in accordance with Example 1 is prepared but additionally contains about 1.0 µg TNF and similarly applied to a cancerous skin lesion and the procedure of Example 1 followed.

EXAMPLE 3

A composition in accordance with Example 1 is prepared but additionally comprises fibronectin in an amount 2.0 μg per gram of composition and the composition similarly applied as in Example 1 to a melanoma skin lesion.

EXAMPLE 4

A composition in the form of an aqueous gel and containing 100 μg of t-PA per gram of composition and 2% by weight of a nonionic surfactant, e.g. nonylphenoxypolyethoxy ethanol, is applied to the skin of a heart attack victim. The amount of skin to which the composition is applied is in the range about 4-20 square inches, preferably at a location close to where the blood clot is located. This application is repeated every 6 hours for at least 2 days and treatment then discontinued. During treatment the patient is subjected to observation and evaluation before a similar such series of treatment might again be initiated.

EXAMPLE 5

A patient having a serious localized full thickness or third degree burn, about 50-200 square centimeters, is treated by generously applying to the burn surface an aqueous gel composition comprising ECGF in an amount of about 15 μg per gram of composition, together with fibronectin in a similar amount. Advantageously, there is also included in the aqueous gel composition a nonionic surfactant, such as nonylphenoxypolyethoxy ethanol, and an antimicrobial agent, such as an antibiotic. The surfactant is employed in an amount of about 5% by weight of the composition and the antibiotic is employed in an amount of about 1% by weight of the composition. About every 6 hours fresh aqueous gel composition containing the above components is applied and this procedure maintained for a number of or days until such time as the patient shows improvement and/or is ready for skin grafting. This procedure is also applicable to the treatment of burn patients having a second degree or an incomplete thickness burn so as to prevent conversion of this burn to a full thickness burn as may be caused by an acquired infection. Also, this procedure is useful for the treatment of wounds, ulcers and the like, and as a postoperative treatment to promote wound healing.

As will be apparent from the above, compositions of this invention provide another approach and technique for, in effect, the systemic treatment of cancer or tumors rather than conventional intravenous chemotherapeutic techniques.

As will be apparent to those skilled in the art in the light of the foregoing disclosure, many changes, modifications and substitutions are possible in the practices of this invention without departing from the spirit or scope thereof.

What is claimed is:

1. A composition suitable for topical or subcutaneous application to a human for the treatment of cancerous or virus-caused skin disorders consisting essentially of a physiologically acceptable carrier, an antiviral or anti-cancer effective amount of a biologically active material selected from the group consisting of tissue plasminogen activator (t-PA), epidermal growth factor (EGF), transforming growth factor-alpha (TGF-α), transforming growth factor-beta (TGF-β), human endothelial cell growth factor (ECGF), granulocyte macrophage colony stimulating factor (GM-CSF), and a fibronectin or large external transformation sensitive protein (LETS) selected from the group of cell surface protein (CSP), cell adhesion protein (CAP), cell insoluble globulin (CIG) and opsonic-alpha 2 surface binding protein, an effective antiviral amount of an antiviral surfactant, an effective antiviral amount of human interferon and an effective amount of an adjuvant to assist in the transdermal transport or transfer of said composition through the skin.

2. A composition in accordance with claim 1 wherein said human interferon is human alpha-interferon.

3. A composition in accordance with claim 1 wherein said antiviral surfactant is a nonionic surfactant.

4. A composition in accordance with claim 1 wherein said antiviral surfactant is nonylphenoxypolyethoxy ethanol.

5. A composition in accordance with claim 1 wherein said adjuvant is dimethylsulfoxide.

6. A composition in accordance with claim 1 wherein said adjuvant is a glycol.

7. A composition in accordance with claim 1 wherein said composition additionally contains an antitumor agent selected from the group consisting of a lymphotoxin, tumor necrosis factor (TNF) and an interleukin.

8. A composition in accordance with claim 1 wherein said carrier is an aqueous gel.

9. A composition in accordance with claim 1 wherein said carrier is an aqueous gel and wherein said antiviral surfactant is present in an amount in the range from about 0.1 to about 20% by weight of said composition.

10. A method for treating cancerous or virus-caused skin disorders of a human which comprises topically or subcutaneously applying a composition consisting essentially of a physiologically acceptable carrier, an antiviral or anti-cancer effective amount of a biologically active material selected from the group consisting of tissue plasminogen (tPA), epidermal growth factor (EGF), transforming growth factor-alpha (TGF-α), transforming growth factor-beta (TGF-β), human endothelial cell growth factor (ECGF) granulocyte macrophage colony stimulating factor (GM-CSF) and a fibronectin or large external transformation sensitive protein (LETS) selected from the group consisting of cell surface protein (CSP), cell adhesion protein (CAP), cell insoluble globulin (CIG), opsonic-alpha 2 surface binding protein, an effective antiviral amount of an antiviral surfactant, an effective antiviral amount of human interferon and an effective amount of an adjuvant to assist in the transdermal transport or transfer of said composition through the skin.

11. A method in accordance with claim 10 wherein said applied composition additionally contains an antitumor agent selected from the group consisting of a lymphotoxin, tumor necrosis factor (TNF) and an interleukin.

12. A method in accordance with claim 10 wherein said physiologically acceptable carrier comprises an aqueous gel, wherein said antiviral surfactant is a nonionic surfactant, wherein said human interferon is human alpha interferon, wherein said adjuvant is selected from the group consisting of dimethylsulfoxide and a glycol and wherein said composition additionally includes an effective amount of an anti-tumor agent selected from the group consisting a lymphotoxin, tumor necrosis factor (TNF) and an interleukin.

* * * * *